United States Patent
Ito et al.

(10) Patent No.: US 12,296,113 B2
(45) Date of Patent: May 13, 2025

(54) CATHETER

(71) Applicant: TERUMO KABUSHIKI KAISHA, Tokyo (JP)

(72) Inventors: Takashi Ito, Shizuoka (JP); Daisuke Shimada, Shizuoka (JP); Kei Ozawa, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 966 days.

(21) Appl. No.: 17/350,481

(22) Filed: Jun. 17, 2021

(65) Prior Publication Data
US 2021/0308416 A1 Oct. 7, 2021

Related U.S. Application Data

(63) Continuation of application No. PCT/JP2020/001215, filed on Jan. 16, 2020.

(30) Foreign Application Priority Data

Jan. 22, 2019 (JP) .................................. 2019-008534

(51) Int. Cl.
*A61M 25/00* (2006.01)
*A61M 25/01* (2006.01)

(52) U.S. Cl.
CPC ...... *A61M 25/005* (2013.01); *A61M 25/0108* (2013.01); *A61M 2210/083* (2013.01); *A61M 2210/086* (2013.01); *A61M 2210/12* (2013.01)

(58) Field of Classification Search
CPC ............ A61M 25/005; A61M 25/0108; A61M 2210/083; A61M 2210/086; A61M 2210/12; A61M 2025/0008
See application file for complete search history.

(56) References Cited

U.S. PATENT DOCUMENTS 5,019,057 A * 5/1991 Truckai ............... A61M 25/005 87/8
2004/0143239 A1 * 7/2004 Zhou ................. A61M 25/0053 604/524

(Continued)

FOREIGN PATENT DOCUMENTS

EP 2 921 194 A1 9/2015
JP H11155956 A 6/1999

(Continued)

OTHER PUBLICATIONS

International Search Report (PCT/ISA/210) with translation and Written Opinion (PCT/ISA/237) mailed on Mar. 24, 2020, by the Japanese Patent Office as the International Searching Authority for International Application No. PCT/JP2020/001215.

(Continued)

*Primary Examiner* — Joel M Attey
*Assistant Examiner* — John A Doubrava
(74) *Attorney, Agent, or Firm* — Buchanan Ingersoll & Rooney PC

(57) ABSTRACT

A catheter having a tubular body including a lumen communicating from a proximal end to a distal end and in which a braided reinforcement body is embedded, and an operation unit disposed on a proximal side of the tubular body. The reinforcement body includes a plurality of first wire filaments helically wound in a first direction of a circumferential direction, toward a distal end direction of the tubular body, and a plurality of second wire filaments intersecting with the first wire filaments and helically wound in a second direction, which is a direction opposite to the first direction. At least one of the first wire filaments is a thick wire filament having a cross section larger than a cross section of a largest second wire filament.

20 Claims, 4 Drawing Sheets

(56) References Cited

U.S. PATENT DOCUMENTS

| | | | |
|---|---|---|---|
| 2009/0030400 A1* | 1/2009 | Bose | A61M 25/0023 604/528 |
| 2012/0199060 A1* | 8/2012 | Furbush, Jr. | A61M 25/09041 116/320 |
| 2015/0265798 A1 | 9/2015 | Nihonmatsu et al. | |

FOREIGN PATENT DOCUMENTS

| | | | | |
|---|---|---|---|---|
| JP | 2006515778 A | 6/2006 | | |
| JP | 2013165926 A | 8/2013 | | |
| JP | 5649131 B2 | 1/2015 | | |
| JP | 2015181503 A | 10/2015 | | |
| WO | WO-9737713 A1 * | 10/1997 | ........ | A61M 25/0012 |
| WO | 2004/064890 A2 | 8/2004 | | |
| WO | 2015146408 A1 | 10/2015 | | |
| WO | 2018092387 A1 | 5/2018 | | |

OTHER PUBLICATIONS

The extended European Search Report issued Feb. 28, 2022, by the European Patent Office in corresponding European Patent Application No. 20744808.5-1132. (9 pages).

* cited by examiner

CATHETER

CROSS-REFERENCES TO RELATED APPLICATIONS

This application is a continuation of International Application No. PCT/JP2020/001215 filed on Jan. 16, 2020, which claims priority to Japanese Patent Application No. 2019-008534, filed on Jan. 22, 2019, the entire content of both of which is incorporated herein by reference.

FIELD OF THE DISCLOSURE

This disclosure relates to a catheter to be inserted into a body lumen.

BACKGROUND DISCUSSION

Currently, intervention is performed, in which treatment of lesion areas such as a heart, a blood vessel, a liver, a brain, a digestive organ, and a urinary organ is performed by a relatively long catheter inserted into the blood vessel from an opening in the skin of a patient.

In recent years, a technique of performing treatment by inserting a catheter from a radial artery of a wrist using a trans radical intervention (TRI) has been widely performed (for example, see WO 2015/146408 A1). Introduction of a catheter from an artery of an arm has an effect of reducing a physical burden on a patient, accelerating discharge of the patient, and the like.

When intravascular treatment from the radial artery to a lower limb region is performed, a catheter having a relatively long effective length is required in order to improve a success rate of a procedure. The effective length is a length of a tubular shaped portion of a catheter in a longitudinal axis direction (i.e., axial direction) that can be inserted into a living body. However, when the effective length is increased while a structure of an existing product is maintained, rotational operability of the catheter is likely to be lost. Since a distal end portion of the catheter reaches a target position while being bent in a relatively long blood vessel, even when a proximal end portion of the catheter is rotated by a hand, the distal end portion of the catheter does not rotate. For this reason, a bifurcated blood vessel cannot be selected, and a delay or failure of the procedure may occur. Therefore, from a market, there is a demand for a catheter that can be rotated even when the effective length is relatively long. In addition, even in a case other than the case where the intravascular treatment from the radial artery to the lower limb region is performed, when a distance from a position to be introduced into the blood vessel to a treatment position is relatively long, a catheter capable of performing a rotating operation is similarly required.

SUMMARY

A catheter is disclosed that indicates a rotatable direction while being capable of improving torque transmission performance in at least one direction of a circumferential direction and helping prevent a decrease in passability.

A catheter is disclosed, which includes a tubular body including a lumen communicating from a proximal end to a distal end and in which a braided reinforcement body is embedded; and an operation unit disposed on a proximal side of the tubular body. The reinforcement body includes: a plurality of first wire filaments helically wound in a first direction of a circumferential direction, toward a distal end direction of the tubular body; and a plurality of second wire filaments intersecting with the first wire filaments and helically wound in a second direction, the second direction being a direction opposite to the first direction. At least one of the first wire filament is a thick wire filament having a cross section larger than a cross section of a largest second wire filament. The operation unit includes a marker that indicates the first direction in a visually and/or tactilely recognizable manner.

In the catheter constituted as described above, since only the first wire filaments wound in the first direction include the thick wire filaments, it is possible to improve torque transmission performance in the first direction more than torque transmission performance in the second direction. In addition, in the catheter, since the thick wire filaments are not included in the second wire filaments, the flexibility is not lost, and the passability in a curved body lumen or the like is not lost. Therefore, the catheter can improve the torque transmission performance in at least one direction of the circumferential direction while preventing a decrease in the passability. In addition, since the marker clearly indicates a rotatable direction, the surgeon can rather easily recognize the first direction having high torque transmission performance.

At least one of the first wire filaments may be a thin wire filament having a cross section equal to or smaller than a size of the cross section of the largest second wire filament. Accordingly, in the catheter, since the first wire filaments include the thin wire filaments, the flexibility is not lost, and it is possible to prevent a decrease in the passability in a curved body lumen or the like.

At least one of the thin wire filaments is disposed in a region between two thick wire filaments adjacent to each other in the circumferential direction of the tubular body, and the number of thin wire filaments disposed in each of the regions arranged in the circumferential direction of the tubular body may be the same. Accordingly, since the thick wire filaments and the thin wire filaments are uniformly disposed in the circumferential direction of the tubular body, it is possible to reduce anisotropy of strength at positions in the circumferential direction of the catheter. Therefore, operability of the catheter can be improved.

The tubular body may include a proximal end tube shaped portion in which the reinforcement body is disposed, and a distal end tube shaped portion disposed on a distal side with respect to the proximal end tube shaped portion and having an outer diameter smaller than an outer diameter of the proximal end tube shaped portion. Therefore, the catheter can improve the torque transmission performance by the proximal end tube shaped portion while maintaining the passability in the stenosed site by the distal end tube shaped portion.

In accordance with an aspect, an effective length of the tubular body may be 1800 mm to 2500 mm. In a normal structure, by applying the thick wire filaments to a catheter having a long effective length in which it is difficult to transmit the torque to the distal end portion, the catheter can improve the torque transmission performance in at least one direction of the circumferential direction while preventing a decrease in the passability.

The catheter may be a catheter to be introduced into a blood vessel from a blood vessel of an arm and inserted into a blood vessel of a lower limb. As a result, the catheter is required to have a relatively long effective length, and is bent, so that an extending direction is folded back in the blood vessel. However, the catheter can reach a target site while preventing a decrease in the passability by applying the thick wire filaments, and can change a direction of the distal end portion by rotating the distal end portion at least in the first direction.

In accordance with an aspect, a catheter is disclosed comprising: a tubular body including a lumen communicating from a proximal end to a distal end; a braided reinforcement body embedded in the tubular body, the braided reinforcement body including a plurality of first wire filaments helically wound in a first direction of a circumferential direction, toward a distal end direction of the tubular body, and a plurality of second wire filaments intersecting with the first wire filaments and helically wound in a second direction, the second direction being a direction opposite to the first direction; and at least one of the plurality of first wire filaments is a thick wire filament having a cross section larger than a cross section of a largest wire filament of the plurality of second wire filaments.

In accordance with another aspect, a catheter is disclosed comprising: an elongated tubular body including a lumen communicating from a proximal end to a distal end, the lumen being open at a distal end opening portion at the distal end of the tubular body; the tubular body includes an inner layer forming an inner surface in the lumen, an outer layer forming an outer surface, and a braided reinforcement body positioned between the inner layer and the outer layer; the braided reinforcement body including a plurality of first wire filaments helically wound in a first direction of a circumferential direction, toward a distal end direction of the tubular body, and a plurality of second wire filaments intersecting with the first wire filaments and helically wound in a second direction, the second direction being a direction opposite to the first direction; at least one of the plurality of first wire filaments is a thick wire filament having a cross section larger than a cross section of a largest wire filament of the plurality of second wire filaments; and an operation unit disposed on a proximal side of the tubular body, and wherein the operation unit includes a marker configured to indicate the first direction in one or more of a visually and tactilely recognizable manner.

DETAILED DESCRIPTION

Figure 1:
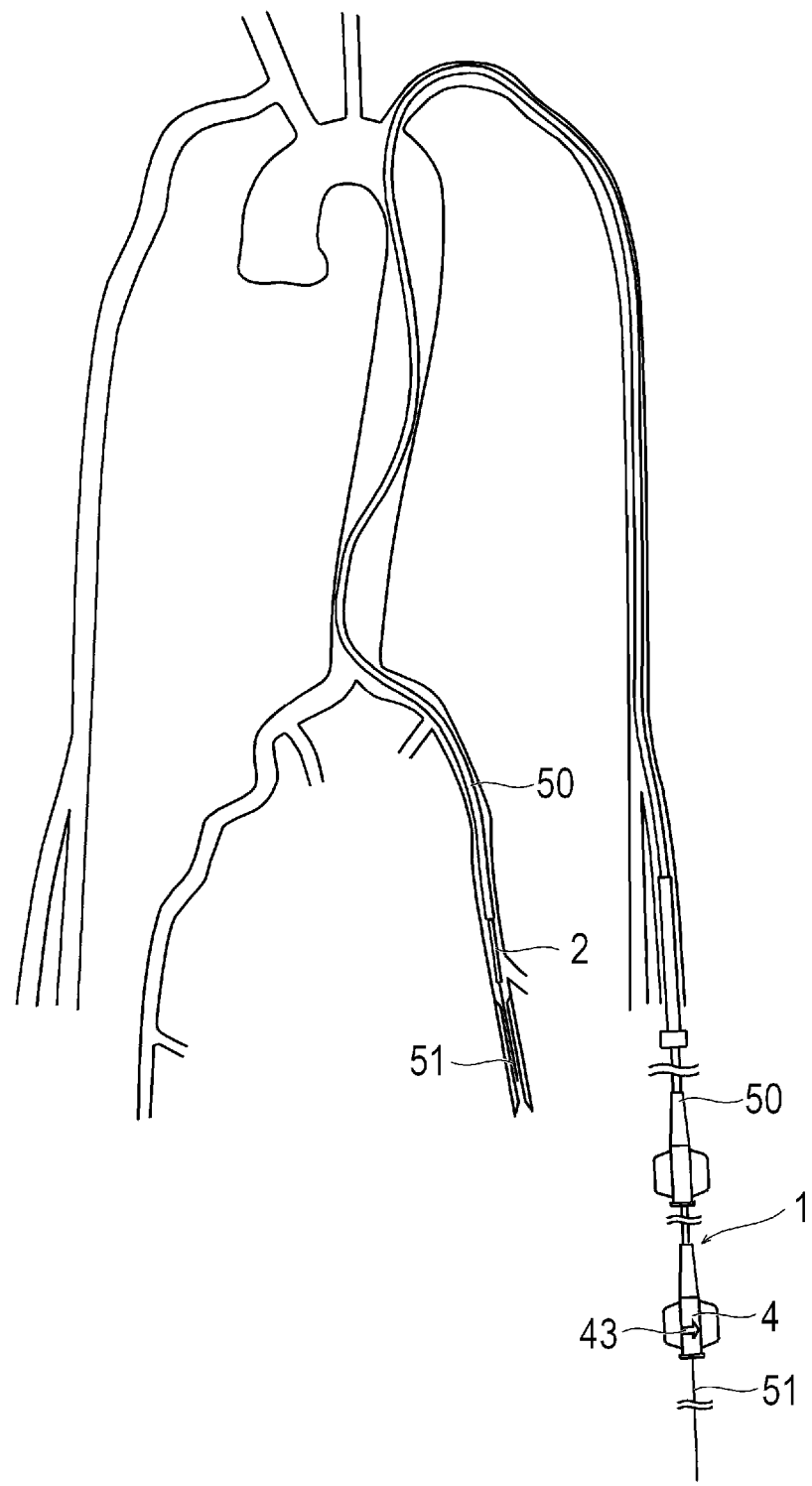
FIG. 1 is a schematic diagram showing an arrangement of a lesion area and a catheter in a blood vessel.

Set forth below with reference to the accompanying drawings is a detailed description of embodiments of a catheter to be inserted into a body lumen representing examples of the inventive catheter. Note that since embodiments described below are preferred specific examples of the present disclosure, although various technically preferable limitations are given, the scope of the present disclosure is not limited to the embodiments unless otherwise specified in the following descriptions. For convenience of explanation, dimensions in the drawings may be exaggerated and may be different from actual dimensions. Further, in present specification and the drawings, structural elements that have substantially the same function are denoted with the same reference numerals, and repeated explanation of these structural elements is omitted. In the present specification, a side to be inserted into a lumen is referred to as a "distal side", and a hand-side to be operated is referred to as a "proximal side".

Figure 2:
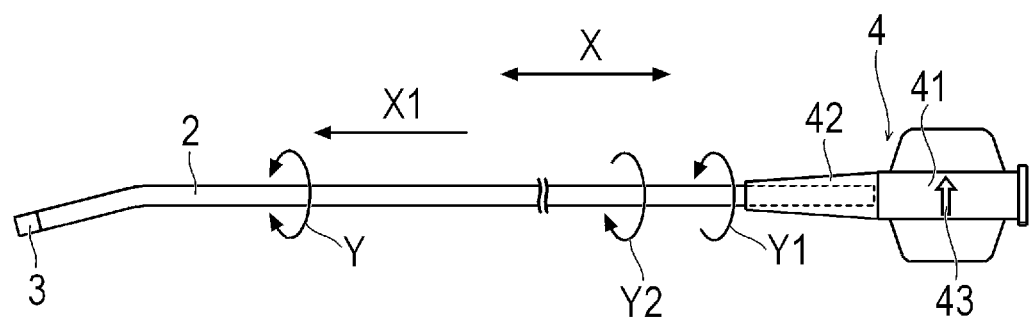
FIG. 2 is a plan view showing a catheter according to an exemplary embodiment.

As shown in FIGS. 1 and 2, a catheter 1 according to the exemplary embodiment is a guide wire support catheter for supporting a guide wire 51, so that the guide wire 51, for example, reaches a blood vessel of a lower limb from a blood vessel of an arm such as a radial artery.

The catheter 1 can include an elongated tubular body 2 and an operation unit 4 provided on a proximal side of the tubular body 2.

Figure 3:
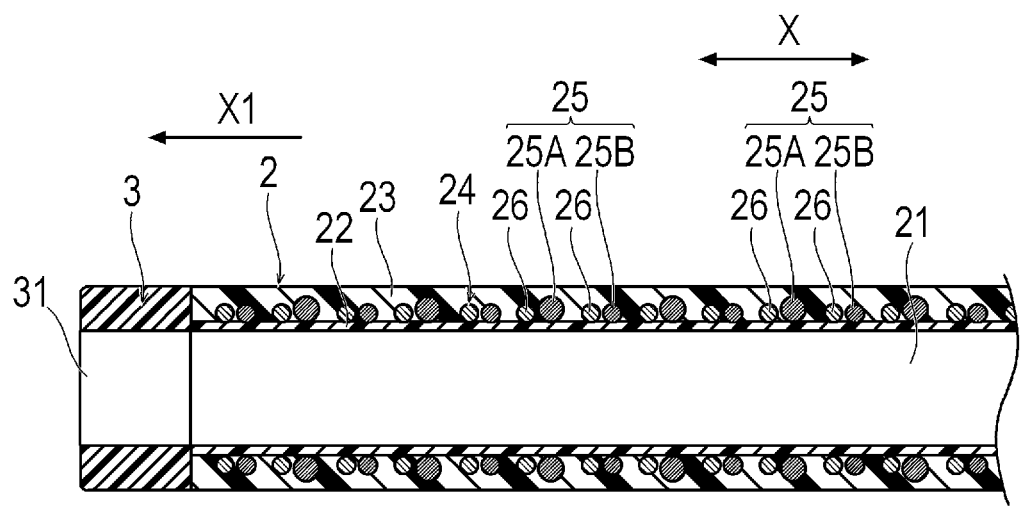
FIG. 3 is a longitudinal sectional view showing a distal end portion of the catheter according to the exemplary embodiment.
Figure 4:
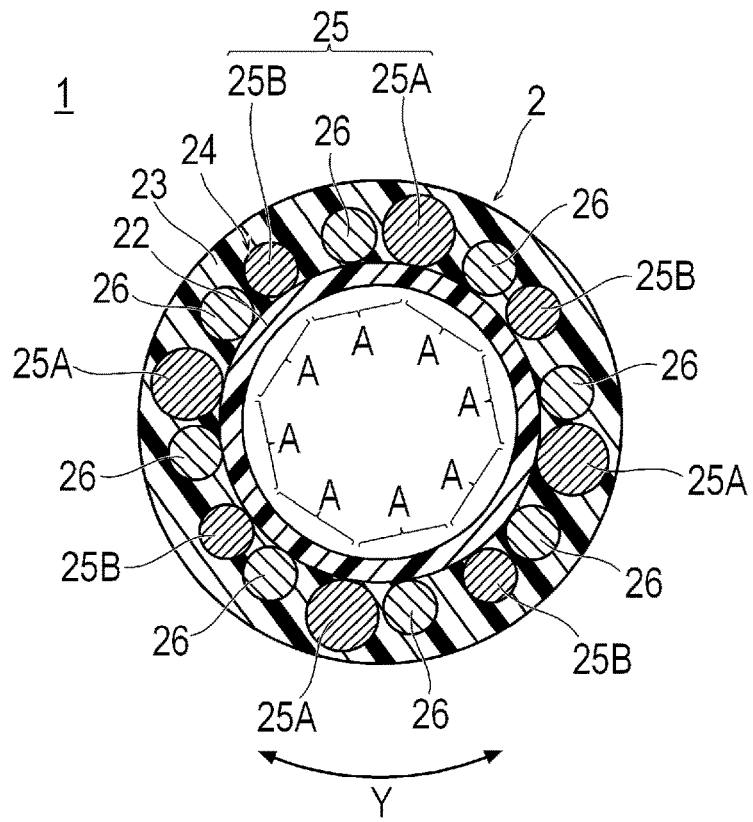
FIG. 4 is a cross-sectional view showing the catheter according to the exemplary embodiment.
Figure 5:
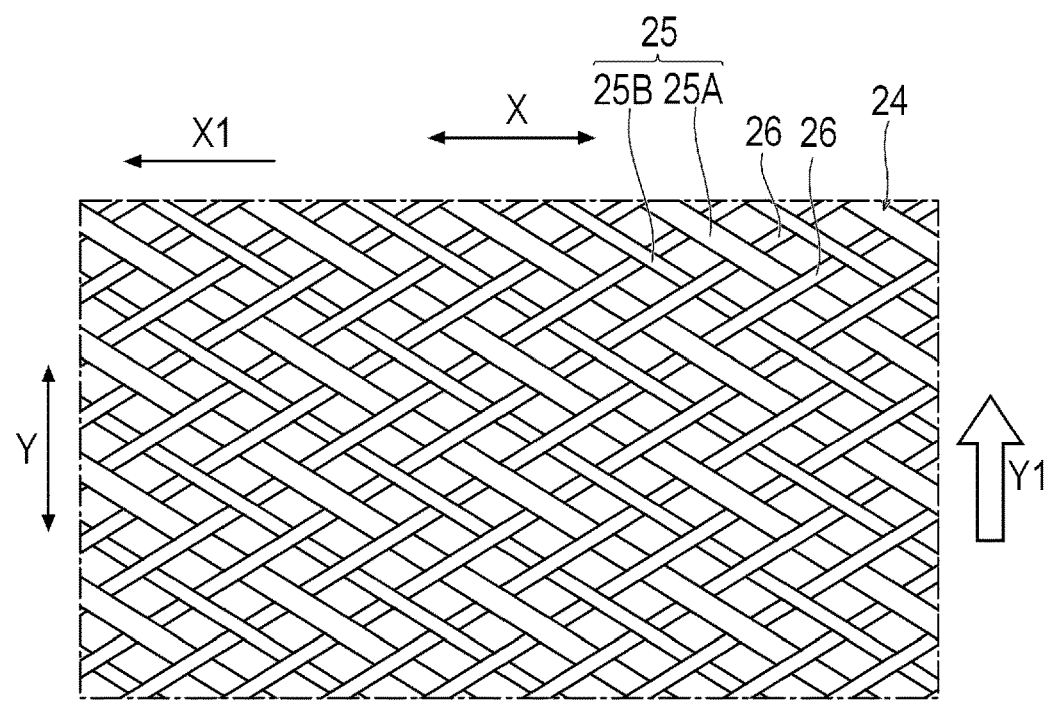
FIG. 5 is a perspective view in which the catheter is developed in a circumferential direction, and wire filaments are observed through an outer layer according to the exemplary embodiment.

As shown in FIGS. 2 to 4, the tubular body 2 is an elongated tubular body having flexibility. A lumen 21 (lumen) communicating from a distal end to a proximal end of the tubular body 2 is formed in a substantially central portion of the tubular body 2. The lumen 21 is open at a distal end opening portion 31 at the distal end of the tubular body 2.

The tubular body 2 includes an inner layer 22 forming an inner surface in the lumen 21, an outer layer 23 forming an outer surface, a reinforcement body 24 positioned between the inner layer 22 and the outer layer 23, and a distal tip 3. The inner layer 22 may extend to the distal tip 3. The distal tip 3 may contain, for example, a metal or the like having radiopacity. Alternatively, the catheter 1 may have a radiopaque marker by which a position in a body can be grasped by embedding a metal wire or a tube having a radiopacity into the catheter 1 or fixing the metal wire or the tube to a surface of the outer layer.

Examples of a constituent material for the outer layer 23 can include various thermoplastic elastomers such as elastomers of styrene-based, polyolefin-based, polyurethane-based, polyester-based, polyimide-based, polybutadiene-based, transpolyisoprene-based, fluororubber-based, and chlorinated polyethylene-based, and one or a combination (polymer alloy, polymer blend, laminate, and the like) of two or more of above elastomers can be used.

A constituent material for the inner layer 22 is preferably a material such that when a medical instrument, for example, such as the guide wire 51 is inserted into the lumen 21, a portion of the inner layer 22 in contact with the medical instrument has relatively low friction. Accordingly, the guide wire 51 inserted into the tubular body 2 can be moved in an axial direction X of the tubular body 2 with a relatively smaller sliding resistance. In accordance with an exemplary embodiment, the entire inner layer 22 may be made of the relatively low-friction material. Examples of the relatively low-friction material can include fluorine-based resin materials such as polytetrafluoroethylene (PTFE).

The inner layer 22 and the outer layer 23 may have an integrated structure made of the same material, or may be formed by disposing materials having different physical properties along the longitudinal axis direction (axial direction) X of the catheter 1.

The reinforcement body 24 reinforces the tubular body 2, and is formed by braiding a plurality of wire filaments with a braider. The resin of the outer layer 23 or the inner layer 22 can enter gaps between the plurality of wire filaments in the reinforcement body 24.

The reinforcement body 24 includes a plurality of first wire filaments 25 and a plurality of second wire filaments 26 intersecting with the first wire filaments 25. The first wire filaments 25 are helically wound in a first direction Y1 of a circumferential direction Y toward a distal end direction X1 of the tubular body 2. The second wire filaments 26 are wound in a second direction Y2, which is a direction opposite to the first direction Y1, of the circumferential direction Y toward the distal end direction X1 of the tubular body 2. The first wire filaments 25 and the second wire filaments 26 intersect with each other by being wound in opposite directions.

In accordance with an exemplary embodiment, for example, among the first wire filaments 25, four are thick wire filaments 25A, and four are thin wire filaments 25B. The thick wire filaments 25A have cross sections larger than those of the thin wire filaments 25B. In the present specification, a size of the cross section of the wire filament means a size of an outer diameter of the wire filament or a size of a cross-sectional area of the wire filament. The outer diameter and the cross-sectional area of the wire filament are an outer diameter and a cross-sectional area in a cross section orthogonal to an axial center of the wire filament. The outer diameter and the cross-sectional area of the wire filament may be an outer diameter and a cross-sectional area in a cross section orthogonal to an axial center of the tubular body 2.

The thick wire filaments 25A are wire filaments having outer diameters larger than outer diameters of all the second wire filaments 26. In addition, the thick wire filaments 25A are wire filaments having cross-sectional areas larger than cross-sectional areas of all the second wire filaments 26. The thin wire filaments 25B are wire filaments that do not satisfy the above-described conditions. That is, the thin wire filaments 25B have outer diameters equal to or smaller than the outer diameter of the second wire filament 26 having a largest outer diameter. The thin wire filaments 25B have cross-sectional areas equal to or smaller than the cross-sectional area of the second wire filament 26 having a largest cross-sectional area.

The outer diameters and the cross-sectional areas of the thick wire filaments 25A are larger than the outer diameters and the cross-sectional areas of the thin wire filaments 25B.

The number of the first wire filaments 25 is not particularly limited, but is eight in the present embodiment. The number of the thick wire filaments 25A and the thin wire filaments 25B is not particularly limited, but in the present embodiment, the number of the thick wire filaments 25A is four, and the number of the thin wire filaments 25B is four.

In accordance with an exemplary embodiment, the number of the thick wire filaments 25A and the number of the thin wire filaments 25B are the same, and may be different. The thick wire filaments 25A and the thin wire filaments 25B are alternately disposed in the circumferential direction Y of the tubular body 2. Therefore, one thin wire filament 25B is disposed in a region A between two thick wire filaments 25A adjacent to each other in the circumferential direction Y. The number of the thin wire filaments 25B disposed in each of the regions A arranged in the circumferential direction Y is the same, and is one in one region A in the present exemplary embodiment, but may be two or more. In addition, the number of the thin wire filaments 25B disposed in the region A may be different depending on the region A. For example, the thin wire filaments 25B may not be disposed in the regions A. In addition, the thin wire filaments 25B may not be present. In accordance with an exemplary embodiment, all of the first wire filaments 25 are the thick wire filaments 25A. The outer diameters (cross-sectional areas) of all of the plurality of thick wire filaments 25A preferably are the same, but may be different depending on the thick wire filaments 25A. The wire filament, for example, may include a plurality of wires.

In accordance with an exemplary embodiment, all of the second wire filaments 26 are wire filaments having the same outer diameters and the same cross-sectional areas. The second wire filaments 26 may each have different outer diameters and/or different cross-sectional areas. The second wire filaments 26 are wire filaments having outer diameters and cross-sectional areas smaller than those of all the thick wire filaments 25A. In accordance with an exemplary embodiment, the number of the second wire filaments 26 is equal to the number of the first wire filaments 25, and may be not equal to the number of the first wire filaments 25 as long as braiding can be performed. The number of the second wire filaments 26 is not particularly limited, for example, the number of second wire filaments 26 is eight in the exemplary embodiment. In the exemplary embodiment, all the second wire filaments 26 and all the thin wire filaments 25B have the same outer diameter and cross-sectional area. All the first wire filaments 25 and the second wire filaments 26 are formed of the same material. Depending on the wire filaments, the first wire filaments 25 and the second wire filaments 26 may have different outer diameters, cross-sectional areas, and the like, and may be made of different materials.

As the constituent material for the first wire filament 25 and the second wire filament 26 can be, for example, a metal material such as stainless steel, NiTi, or tungsten. The number of the first wire filaments 25 and the second wire filaments 26 is not particularly limited. Cross-sectional shapes of the first wire filaments 25 and the second wire filaments 26 are not limited to a circle, and may be, for example, an ellipse, a square, a rectangle, an oval, or the like.

In accordance with an exemplary embodiment, since the catheter 1 can include such a reinforcement body 24, sufficient rigidity and strength can be secured without increasing a wall thickness of the tubular body 2. As a result, the catheter 1 can have an inner diameter, for example, configured to allow a medical instrument such as the guide wire 51 to be inserted in the inner diameter of the catheter and an outer diameter capable of being inserted into a relatively thin blood vessel. Further, the catheter 1 can have excellent pushability and torque transmission performance.

The outer diameters of the thin wire filaments 25B and the second wire filaments 26 are not particularly limited, but can be, for example, 0.04 mm to 0.05 mm. The outer diameters of the thick wire filaments 25A are not particularly limited, but can be, for example, 0.10 mm to 0.20 mm. Alternatively, at least a part of the outer diameters of the thick wire filaments 25A may be equal to or larger than the outer diameters of the thin wire filaments 25B, and preferably, for example, 0.02 mm to 0.05 mm larger than the outer diameters of the thin wire filaments 25B. A braid pitch of reinforcement wires (the thin wire filaments 25B and the second wire filaments 26) can be, for example, 0.4 mm to 0.8 mm, and may be constant in the longitudinal axis direction or may be changed in the longitudinal axis direction.

An inner diameter of the tubular body 2 is not particularly limited, and the inner diameter can be, for example, 0.4 mm to 3 mm, and for example, preferably 0.4 mm to 1.1 mm. An outer diameter of the tubular body 2 is not particularly limited, and the outer diameter can be, for example, 0.7 mm to 3.2 mm, for example, preferably 0.6 mm to 2.1 mm, and can be more preferably 1.65 mm in a case where the catheter 1 is a 5 Fr catheter. An inner diameter or an outer diameter of the proximal end may be larger than that of the distal end.

In accordance with an exemplary embodiment, an effective length of the tubular body 2 can be, for example, 1500 mm to 3000 mm, preferably 1800 mm to 2500 mm, and more preferably 2300 mm. The effective length is a length in the axial direction X from a distal-most end of the operation unit 4 (a distal-most end of an anti-kink protector 42) to a distal-most end of the tubular body 2 (a distal-most end of the distal tip 3).

An angle of each of the first wire filaments 25 and the second wire filaments 26 with respect to the axial direction X of the tubular body 2 is not particularly limited, and can be, for example, 20° to 70°. The angle may vary depending on a position of the tubular body 2 in the longitudinal axis direction X.

The number of layers constituting the tubular body 2, a constituent material of each layer, a presence or absence of a wire filament, and the like may be different along the longitudinal axis direction of the tubular body 2. For example, in order to provide higher flexibility on a portion of the distal side of the tubular body 2, the number of layers may be reduced, a more flexible material may be used, or the reinforcement body 24 may not be disposed only in the portion.

At least a part of the tubular body 2 may be curved. Since the tubular body 2 is curved, depending on applications of the catheter 1, it is possible to form a shape suitable for a site to be inserted, or to rather easily direct the catheter 1 or the guide wire 51 to a target site.

The distal tip 3 shown in FIGS. 2 and 3 is a tube shaped member disposed on the distal side of the tubular body 2. The distal tip 3 can be made of a relatively highly flexible material such as a rubber material. Since the catheter 1 includes the distal tip 3, the catheter 1 can travel rather smoothly and safely even in a curved, bent, or bifurcated blood vessel.

At least a part of an outer surface of the catheter 1 may be coated with a lubricating resin in order to improve passability of a stenosed site in the blood vessel. For example, the lubricating resin (i.e., coating resin) can be preferably a hydrophilic lubricating resin, and more preferably a portion of the distal end portion of the catheter 1 is coated with the coating resin.

As shown in FIG. 2, the operation unit 4 is disposed at the proximal end of the tubular body 2. The operation unit 4 can include a hub 41 and the anti-kink protector 42. A passage communicating with the lumen 21 is formed in the hub 41. A marker 43 allowing the first direction Y1 to be visually recognized is formed on an outer peripheral surface of the hub 41. The marker 43 can be, for example, an arrow directing the first direction Y1. The marker 43 can indicate, for example, the first direction Y1 by a color, a shape such as a convex portion and a concave portion, a character, or a symbol. The marker 43 may allow the first direction Y1 to be tactilely recognized.

Figure 7:
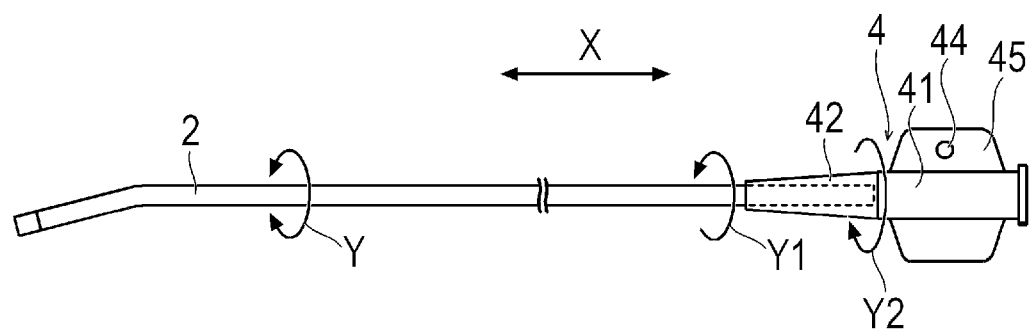
FIG. 7 is a plan view showing the modification of the catheter according to the exemplary embodiment.

As in a modification shown in FIG. 7, the operation unit 4 may include a marker 44 that can be tactilely recognized on a wing unit 45 of the hub 41. The wing unit 45 protrudes outward in a radial direction of the operation unit 4. For example, the wing unit 45 provided with the marker 44 is directed to an upper side in a vertical direction, and the marker 44 is disposed at a position directed to a surgeon side. That is, the wing unit 45 has a surface facing to the second direction Y2 which is a direction opposite to the first direction Y1, and the marker 44 such as a convex portion or a concave portion which can be tactilely recognized is formed on the surface facing to the second direction Y2 which is a direction opposite to the first direction Y1. In a case where the catheter 1 is rotatable in a clockwise direction (the first direction Y1) as the distal end is viewed from a hand, when the hub 41 is rotated in the clockwise direction, the catheter 1 can be operated by tactilely recognizing the marker 44 without looking at the hand. As a result, it is possible to prevent an erroneous operation due to an error in a rotation direction of the catheter 1 and to help shorten a surgical time.

For example, the guide wire 51 can be inserted into or removed from the hub 41, or various liquids such as a contrast agent (radiopaque agent), a drug solution, and a saline solution can be injected from the hub 41.

The anti-kink protector 42 can be made of an elastic material. The anti-kink protector 42 covers a portion connecting the tubular body 2 and the hub 41, thereby preventing the tubular body 2 from bending (kinking) in a vicinity of the portion connecting the tubular body 2 and the hub 41. The marker 43 may be formed not on the hub 41 but on the anti-kink protector 42.

Next, operations of the catheter 1 according to the exemplary embodiment will be described.

As shown in FIG. 1, the catheter 1 is inserted from a blood vessel of an arm into a blood vessel via a guiding catheter 50, and is pushed into a blood vessel of a lower limb. The blood vessel of the arm is an artery, for example, a radial artery, and may be an ulnar artery, an upper arm artery, or the like. The blood vessel of the lower limb is an artery on an ending side with respect to a bifurcated portion bifurcating from an abdominal aorta to a common iliac artery, and can be, for example, an iliac artery, or a superficial femoral artery. The catheter 1 is bent so as to be folded back in a vicinity of a site where a subclavian artery and a thoracic aorta are connected to each other, and is pushed to the lower limb. The distal end portion and a proximal end portion of the tubular body 2 of the catheter 1 may be directed in substantially opposite directions. When selecting a blood vessel to be inserted or the like, a surgeon manually operates the operation unit 4 to rotate the operation unit 4 in the first direction Y1 indicated by the marker 43, as shown in FIGS. 2 to 5. The thick wire filaments 25A disposed in the tubular body 2 are wound in the first direction Y1 toward the distal end direction X1. Therefore, the thick wire filaments 25A resist torque acting on the tubular body 2 from the proximal side so as to stretch. Therefore, the tubular body 2 is resistant to twisting in the first direction Y1, and torque acting on the operation unit 4 in the first direction Y1 can be effectively transmitted to the distal end portion. Therefore, the surgeon can direct the distal end portion of the tubular body 2 in a desirable direction. As a result, the surgeon can rather easily insert the distal end portion of the tubular body 2 into the blood vessel to be inserted in a relatively short time. When the surgeon rotates the operation unit 4 in the second direction Y2 opposite to the first direction Y1 indicated by the marker 43, the tubular body 2 cannot effectively transmit the torque to the distal end portion. However, as long as the catheter 1 can be rotated in the first direction Y1, even when the catheter 1 cannot be rotated in the second direction Y2, the distal end portion of the catheter 1 can be directed in all directions over 360 degrees. In addition, since the outer diameters of all the second wire filaments 26 intersecting the thick wire filaments 25A are smaller than the outer diameters of the thick wire filaments 25A, the catheter 1 can be made relatively flexible even though the catheter 1 has the thick wire filaments 25A, which are relatively rigid. Further, since a half of the first wire filaments 25 are the thin wire filaments 25B having rigidity lower than that of the thick wire filaments 25A, the catheter 1 can be made relatively flexible even though the catheter 1 has the thick wire filaments 25A.

Therefore, the catheter 1 can avoid blood vessel injury without weakening the passability in a thin and curved blood vessel.

As described above, the catheter 1 according to the exemplary embodiment can include the tubular body 2 including the lumen communicating from the proximal end to the distal end and in which the braided reinforcement body 24 is embedded; and the operation unit 4 disposed on the proximal side of the tubular body 2. The reinforcement body 24 can include the plurality of first wire filaments 25 helically wound in the first direction Y1 of the circumferential direction Y, toward the distal end direction X1 of the tubular body 2; and the plurality of second wire filaments 26 intersecting with the first wire filaments 25 and helically wound in the second direction Y2, which is a direction opposite to the first direction Y1. At least one of the first wire filaments 25 is the thick wire filament 25A having a cross section larger than a cross section of a largest second wire filament 26. The operation unit 4 can include the marker 43 that indicates the first direction Y1 in a visually and/or tactilely recognizable manner.

In the catheter 1 as described above, since only the first wire filaments 25 wound in the first direction Y1 include the thick wire filaments 25A, it is possible to improve torque transmission performance in the first direction Y1 more than torque transmission performance in the second direction Y2. In addition, in the catheter 1, since the thick wire filaments 25A are not included in the second wire filaments 26, the flexibility is not lost, and the passability in a curved body lumen or the like is also not lost. Therefore, the catheter 1 can improve the torque transmission performance in at least the first direction X1 of the circumferential direction Y while preventing a decrease in the passability. The catheter 1 may also improve the torque transmission performance in the second direction Y2, though not as much as the torque transmission performance in the first direction Y1. In addition, since the marker 43 indicates a rotatable direction, the surgeon can rather easily recognize the first direction Y1 having high torque transmission performance. Therefore, operability of the catheter 1 can be improved.

At least one of the first wire filaments 25 is a thin wire filament 25B having a cross section equal to or smaller than a size of the cross section of the largest second wire filament 26. Accordingly, in the catheter 1, since the first wire filaments 25 include the thin wire filaments 25B that are not the thick wire filaments 25A, the flexibility is not lost, and it is possible to help prevent a decrease in the passability in a curved body lumen or the like.

In addition, at least one of the thin wire filaments 25B is disposed in a region A between two thick wire filaments 25A adjacent to each other in the circumferential direction Y of the tubular body 2, and the number of thin wire filaments 25B disposed in each of the regions A arranged in the circumferential direction Y of the tubular body 2 is the same. Accordingly, since the thick wire filaments 25A and the thin wire filaments 25B are uniformly disposed in the circumferential direction Y of the tubular body 2, it is possible to reduce anisotropy of strength at positions in the circumferential direction Y of the catheter 1. Therefore, the operability of the catheter 1 can be improved.

The effective length of the tubular body 2 may be, for example, 1800 mm to 2500 mm. The effective length of the tubular body 2 being the length of the tubular body insertable into the blood vessel, for example, from a distal end of the anti-kink protector 42 to a distal end opening portion 31 at the distal end of the tubular body 2. In a normal structure, by applying the thick wire filaments 25A to the catheter 1 having a relatively long effective length in which it is difficult to transmit the torque to the distal end portion, the catheter 1 can improve the torque transmission performance in the first direction Y1 while preventing a decrease in the passability.

In addition, the catheter 1 as disclosed is introduced into a blood vessel from a blood vessel of an arm and inserted into a blood vessel of a lower limb. As a result, the catheter 1 can be required to have a relatively long effective length, and can be bent, so that an extending direction is folded back in the blood vessel. However, the catheter 1 can reach the target site while preventing a decrease in the passability by applying the above-described thick wire filaments 25A, and can change a direction of the distal end portion by rotating the distal end portion at least in the first direction Y1. In addition, since the catheter 1 is introduced from a blood vessel of an arm having relatively low invasiveness, it is possible to shorten a compression time of an introduction portion (cut-out portion) of a blood vessel and a bedridden time after surgery, and it is possible to reduce a burden on a patient.

Note that this disclosure is not limited to the embodiment described above, and various modifications can be made by those skilled in the art within a scope of the technical idea of this disclosure. For example, the blood vessel into which the catheter 1 is introduced is not limited to a blood vessel of an arm, and may be a blood vessel of a lower limb such as a femoral artery. The target site to which the catheter 1 reaches is not limited to the blood vessel of the lower limb, and may be, for example, a blood vessel of a heart or a brain. The application of the catheter 1 is not particularly limited as long as the catheter 1 is used by being inserted into a body lumen. The body lumen is not limited to a blood vessel, and may be, for example, a vessel, a urinary duct, a bile duct, a fallopian tube, or a hepatic duct.

In addition, the tubular body 2 may be configured such that the flexibility gradually increases in the distal end direction X1. Accordingly, when the insertion operation into the blood vessel is performed, the insertion operation into the blood vessel can be performed safely while sufficiently ensuring the pushability and the torque transmission performance in the distal end direction X1. In order to gradually increase the flexibility of the tubular body 2 toward the distal end direction X1, the outer layer 23 and the inner layer 22 can be divided into a plurality of regions in the axial direction X, and the shape and the material can be changed, or a dimension and a pitch of the wire filament can be changed, so that the region on the distal side is more flexible.

Figure 6:
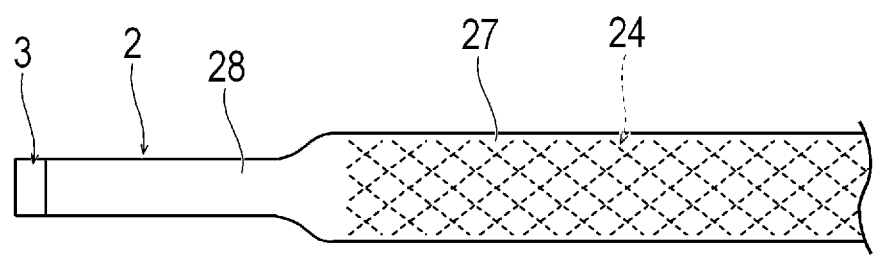
FIG. 6 is a plan view showing a modification of the catheter according to the exemplary embodiment.

In addition, as in the modification shown in FIG. 6, the tubular body 2 may include a proximal end tube shaped portion 27 in which the reinforcement body 24 is disposed, and a distal end tube shaped portion 28 on a distal side of the proximal end tube shaped portion 27 and in which the reinforcement body 24 is not disposed. The distal end tube shaped portion 28 may be formed to have the same outer diameter and inner diameter as those of the proximal end tube shaped portion 27 in which the reinforcement body 24 is disposed, or may be formed to have an outer diameter and/or an inner diameter smaller than those of the proximal end tube shaped portion 27. Since the reinforcement body 24 with the thick wire filaments 25A is disposed, the tubular body 2 becomes thick, and the passability in the stenosed site may be reduced. In accordance with an exemplary embodiment, by appropriately setting a length of the proximal end tube shaped portion 27 and a length of the distal end tube shaped portion 28 along the axial direction X, the flexibility and the passability of the tubular body 2 can be appropriately set. That is, the catheter 1 can improve the torque transmission performance by the proximal end tube shaped portion 27 while maintaining the passability in the stenosed site by the distal end tube shaped portion 28.

In addition, in a configuration in which only the second wire filaments 26 wound in the second direction Y2 include thick wire filaments, the torque transmission performance in the second direction Y2 may be more than that in the first direction Y1.

The detailed description above describes embodiments of a catheter to be inserted into a body lumen. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
    a tubular body including a lumen communicating from a proximal end to a distal end and in which a braided reinforcement body is embedded;
    an operation unit disposed on a proximal side of the tubular body;
    the braided reinforcement body including a plurality of first metal wire filaments helically wound in a first direction of a circumferential direction, toward a distal end direction of the tubular body, and a plurality of second metal wire filaments intersecting with the first metal wire filaments and helically wound in a second direction, the second direction being a direction opposite to the first direction;
    at least one of the plurality of first metal wire filaments is a thick wire filament having a cross section larger than a cross section of a largest wire filament of the plurality of second metal wire filaments;
    at least one of the plurality of first metal wire filaments is a thin wire filament having a cross section equal to or smaller than a size of the cross section of the largest wire filament of the plurality of second metal wire filaments; and
    wherein the operation unit includes a marker configured to indicate the first direction in one or more of a visually and tactilely recognizable manner.

2. The catheter according to claim 1, wherein the thin wire filament is disposed between adjacent thick wire filaments in the circumferential direction of the tubular body.

3. The catheter according to claim 1, wherein the tubular body includes a proximal end tube shaped portion in which the braided reinforcement body is disposed, and a distal end tube shaped portion disposed on a distal side with respect to the proximal end tube shaped portion and having an outer diameter smaller than an outer diameter of the proximal end tube shaped portion.

4. The catheter according to claim 1, wherein an effective length of the tubular body is 1800 mm to 2500 mm.

5. The catheter according to claim 1, wherein the catheter is a catheter configured to be introduced into a blood vessel from a blood vessel of an arm and inserted into a blood vessel of a lower limb.

6. The catheter according to claim 1, wherein the tubular body includes an inner layer forming an inner surface of the lumen and an outer layer, and wherein the braided reinforcement body is positioned between the inner layer and the outer layer.

7. The catheter according to claim 1, wherein the plurality of first metal wire filaments is eight and the plurality of second metal wire filaments is eight, and the plurality of first metal wire filaments includes four thick wire filaments and four less thick wire filaments.

8. The catheter according to claim 1, wherein the plurality of first metal wire filaments has a braid pitch of 0.4 mm to 0.8 mm and the plurality of second metal wire filaments has a braid pitch of 0.4 mm to 0.8 mm.

9. The catheter according to claim 1, wherein the cross section of the at least one of the plurality of first metal wire filaments is smaller than the size of the cross section of the largest wire filament of the plurality of second metal wire filaments.

10. The catheter according to claim 1, wherein the cross section of the at least one of the plurality of first metal wire filaments is equal to the size of the cross section of the largest wire filament of the plurality of second metal wire filaments.

11. The catheter according to claim 1, wherein torque transmission performance in the first direction is greater than torque transmission performance in the second direction.

12. The catheter according to claim 1, wherein the plurality of first metal wire filaments and the plurality of second metal wire filaments are stainless steel, nickel-titanium (NiTi), or tungsten.

13. The catheter according to claim 6, wherein the tubular body includes a distal tip, the distal tip containing a metal material having radiopacity.

14. The catheter according to claim 7, wherein an outer diameter of each of the four thick wire filaments is 0.10 mm to 0.20 mm, an outer diameter of each of the four less thick wire filaments is 0.04 mm to 0.05 mm, and an outer diameter of the largest wire filament of the plurality of second metal wire filaments is 0.04 mm to 0.05 mm.

15. A catheter comprising:
    a tubular body including a lumen communicating from a proximal end to a distal end;
    a braided reinforcement body embedded in the tubular body, the braided reinforcement body including a plurality of first metal wire filaments helically wound in a first direction of a circumferential direction, toward a distal end direction of the tubular body, and a plurality of second metal wire filaments intersecting with the first metal wire filaments and helically wound in a second direction, the second direction being a direction opposite to the first direction;
    at least one of the plurality of first metal wire filaments is a thick wire filament having a cross section larger than a cross section of a largest wire filament of the plurality of second metal wire filaments; and
    wherein at least one of the plurality of first metal wire filaments is a thin wire filament having a cross section equal to or smaller than a size of the cross section of the largest wire filament of the plurality of second metal wire filaments.

16. The catheter according to claim 15, wherein the thin wire filament is disposed between adjacent thick wire filaments in the circumferential direction of the tubular body.

17. The catheter according to claim 15, wherein the tubular body includes a proximal end tube shaped portion in which the braided reinforcement body is disposed, and a distal end tube shaped portion disposed on a distal side with respect to the proximal end tube shaped portion and having an outer diameter smaller than an outer diameter of the proximal end tube shaped portion.

18. A catheter comprising:
- an elongated tubular body including a lumen communicating from a proximal end to a distal end, the lumen being open at a distal end opening portion at the distal end of the tubular body;
- the tubular body includes an inner layer forming an inner surface in the lumen, an outer layer forming an outer surface, and a braided reinforcement body positioned between the inner layer and the outer layer;
- the braided reinforcement body including a plurality of first metal wire filaments helically wound in a first direction of a circumferential direction, toward a distal end direction of the tubular body, and a plurality of second metal wire filaments intersecting with the first metal wire filaments and helically wound in a second direction, the second direction being a direction opposite to the first direction;
- at least one of the plurality of first metal wire filaments is a thick wire filament having a cross section larger than a cross section of a largest wire filament of the plurality of second metal wire filaments;
- at least one of the plurality of first metal wire filaments is a thin wire filament having a cross section equal to or smaller than a size of the cross section of the largest wire filament of the plurality of second metal wire filaments; and
- an operation unit disposed on a proximal side of the tubular body, and wherein the operation unit includes a marker configured to indicate the first direction in one or more of a visually and tactilely recognizable manner.

19. The catheter according to claim 18, wherein the thin wire filament is disposed between adjacent thick wire filaments in the circumferential direction of the tubular body.

20. The catheter according to claim 18, wherein the tubular body includes a proximal end tube shaped portion in which the braided reinforcement body is disposed, and a distal end tube shaped portion disposed on a distal side with respect to the proximal end tube shaped portion and having an outer diameter smaller than an outer diameter of the proximal end tube shaped portion.

* * * * *